United States Patent
Levy et al.

(10) Patent No.: US 11,291,866 B2
(45) Date of Patent: Apr. 5, 2022

(54) ULTRASOUND FOCUSING IN DYNAMICALLY CHANGING MEDIA

(71) Applicants: Yoav Levy, Hinanit (IL); Eyal Zadicario, Tel Aviv-Jaffa (IL); Shuki Vitek, Haifa (IL); Javier Grinfeld, Tel Aviv-Jaffa (IL); Ohad Silbiger, Zichron Yaakov (IL)

(72) Inventors: Yoav Levy, Hinanit (IL); Eyal Zadicario, Tel Aviv-Jaffa (IL); Shuki Vitek, Haifa (IL); Javier Grinfeld, Tel Aviv-Jaffa (IL); Ohad Silbiger, Zichron Yaakov (IL)

(73) Assignee: INSIGHTEC, LTD., Tirat Carmel (IL)

( * ) Notice: Subject to any disclaimer, the term of this patent is extended or adjusted under 35 U.S.C. 154(b) by 790 days.

(21) Appl. No.: 15/837,365

(22) Filed: Dec. 11, 2017

(65) Prior Publication Data

US 2019/0175954 A1    Jun. 13, 2019

(51) Int. Cl.
*A61B 8/00* (2006.01)
*A61B 8/08* (2006.01)
(Continued)

(52) U.S. Cl.
CPC ............ *A61N 7/022* (2013.01); *A61B 8/0808* (2013.01); *A61B 8/4488* (2013.01);
(Continued)

(58) Field of Classification Search
None
See application file for complete search history.

(56) References Cited

U.S. PATENT DOCUMENTS

| | | | |
|---|---|---|---|
| 9,022,939 B2 * | 5/2015 | Hall | A61B 8/481 600/458 |
| 2004/0059265 A1 | 3/2004 | Candy et al. | |

(Continued)

FOREIGN PATENT DOCUMENTS

| | | |
|---|---|---|
| GB | 2515134 A | 12/2014 |
| WO | 2015200576 A1 | 12/2015 |

(Continued)

OTHER PUBLICATIONS

Wang et al. (Ultrasound and Microbubble guided drug delivery: Mechanistic Understanding and Clinical Implications, Current Pharmaceutical Biotech. vol. 14, No. 8, 2014 (Year: 2014).*

(Continued)

*Primary Examiner* — Amelie R Davis
*Assistant Examiner* — Marjan Saboktakin
(74) *Attorney, Agent, or Firm* — Morgan, Lewis & Bockius LLP

(57) ABSTRACT

Various approaches to generating and maintaining an ultrasound focus at a target region include configuring a controller to cause transmission of treatment ultrasound pulses from a transducer having multiple transducer elements; cause the transducer to transmit focusing ultrasound pulses to the target region and generate an acoustic reflector therein; measure reflections of the focusing ultrasound pulses from the acoustic reflector; based at least in part on the measured reflections, adjust a parameter value associated with one or more transducer elements so as to maintain and/or improve the ultrasound focus at the target region.

27 Claims, 10 Drawing Sheets

(51) Int. Cl.
- *G01S 15/89* (2006.01)
- *G01S 7/52* (2006.01)
- *A61B 5/01* (2006.01)
- *A61B 5/055* (2006.01)
- *A61N 7/02* (2006.01)
- *A61N 7/00* (2006.01)
- *A61B 17/22* (2006.01)
- *A61B 34/10* (2016.01)

(52) U.S. Cl.
CPC ............ *A61B 8/4494* (2013.01); *A61B 8/481* (2013.01); *A61B 8/585* (2013.01); *A61N 7/00* (2013.01); *A61N 7/02* (2013.01); *G01S 7/5205* (2013.01); *G01S 7/52039* (2013.01); *G01S 15/8925* (2013.01); *A61B 5/015* (2013.01); *A61B 5/055* (2013.01); *A61B 2017/22007* (2013.01); *A61B 2034/104* (2016.02); *A61B 2034/105* (2016.02); *A61N 2007/003* (2013.01); *A61N 2007/0021* (2013.01); *A61N 2007/0039* (2013.01); *A61N 2007/0043* (2013.01); *A61N 2007/0052* (2013.01); *A61N 2007/0073* (2013.01); *A61N 2007/0078* (2013.01); *A61N 2007/0091* (2013.01); *A61N 2007/0095* (2013.01); *A61N 2007/027* (2013.01); *G01S 15/89* (2013.01); *G01S 15/8927* (2013.01)

(56) References Cited

U.S. PATENT DOCUMENTS

2014/0316269 A1* 10/2014 Zhang ................. A61N 7/02 600/439
2016/0184026 A1* 6/2016 Tlusty ................. A61B 19/00
2016/0339273 A1* 11/2016 Al Mayiah ............. A61N 7/02

FOREIGN PATENT DOCUMENTS

WO WO-2015200576 A1 * 12/2015 ........ A61M 37/0092
WO 2018020315 A1 2/2018

OTHER PUBLICATIONS

Tzu-Yin Wang et al: "Ultrasound and Microbubble Guided Drug Delivery: Mechanistic Understanding and Clinical Implications", Current Pharmaceutical Biotechnology, vol. 14. No. 8, Jan. 31, 2014 (Jan. 31, 2014), pp. 743-752.

International Search Report and the Written Opinion for international application No. PCT/IB2018/001525 dated Apr. 23, 2019 16 pages.

Haworth et al: "Towards Aberration Correction of Transcranial Ultrasound Using Acoustic Droplet Vaporization". Ultrasound in Medicine and Biology, New York. NY. US. vol. 34. No. 3. Oct. 23, 2007 (Oct. 23, 2007), pp. 435-445.

* cited by examiner

ULTRASOUND FOCUSING IN DYNAMICALLY CHANGING MEDIA

FIELD OF THE INVENTION

The present invention relates, generally, to systems and methods for ultrasound focusing and, more particularly, to focusing through a medium in which the acoustic properties may dynamically change.

BACKGROUND

Focused ultrasound (i.e., acoustic waves having a frequency greater than about 20 kiloHertz) can be used to image or therapeutically treat a patient's internal body tissues. For example, ultrasound waves may be used in applications involving ablation of tumors, thereby eliminating the need for invasive surgery, targeted drug delivery, control of the blood-brain barrier, lysing of clots, and other surgical procedures. During tumor ablation, a piezoceramic transducer is placed externally to the patient, but in close proximity to the tissue to be ablated (i.e., the target). The transducer converts an electronic drive signal into mechanical vibrations, resulting in the emission of acoustic waves. The transducer may be geometrically shaped and positioned along with other such transducers so that the ultrasound energy they emit collectively forms a focused beam at a "focal zone" corresponding to (or within) the target tissue region. Alternatively or additionally, a single transducer may be formed of a plurality of individually driven transducer elements whose phases can each be controlled independently. Such a "phased-array" transducer facilitates steering the focal zone to different locations by adjusting the relative phases among the transducers. As used herein, the term "element" means either an individual transducer in an array or an independently drivable portion of a single transducer. Magnetic resonance imaging (MRI) may be used to visualize the patient and target, and thereby to guide the ultrasound beam.

The noninvasive nature of ultrasound surgery is particularly appealing for the treatment of brain tumors. However, the human skull has been a barrier to the clinical realization of ultrasound therapy. Impediments to transcranial ultrasound procedures include strong attenuation and the distortions caused by irregularities in the skull's shape, density, and sound speed, which contribute toward destroying the focus and/or decreasing the ability to spatially register received diagnostic information.

To the overcome difficulties imposed by the human skull, one conventional approach measures phase shifts resulting from travel of an ultrasound beam through the skull and subsequently adjusts ultrasound parameters to account for the aberrations caused at least in part by the skull. For example, a minimally invasive approach uses receiving probes designed for catheter insertion into the brain to measure the amplitude and phase distortion caused by the skull. Catheter insertions, however, still require surgery, which can be painful and can create a risk of infection.

An alternative, completely noninvasive approach uses X-ray computed tomography (CT) images, rather than receiving probes, to predict the wave distortion caused by the skull. In practice, however, computations of the relative phases alone may too be imprecise to enable high-quality focusing. For example, when ultrasound is focused into the brain to treat a tumor, the skull in the acoustic path may cause aberrations that are not readily ascertainable. In such situations, treatment is typically preceded by a focusing procedure in which an ultrasound focus is generated at or near the target, the quality of the focus is measured (using, e.g., thermal imaging or acoustic radiation force imaging (ARFI)), and experimental feedback is used to adjust the phases of the transducer elements to achieve sufficient focus quality.

This focusing procedure, however, may take a substantial amount of time, which may render it impracticable or, at the least, inconvenient for a patient. In addition, the procedure itself can alter acoustic properties and further complicate efforts to compensate. In particular, during the procedure, ultrasound energy is inevitably deposited into the intervening tissue (e.g., the cortexes and marrow) located between the target and the transducer; this may cause a temperature increase in the intervening tissue, which, in turn, changes its acoustic properties. Consequently, the wave attenuations and distortions caused by the intervening tissue may vary as the ultrasound treatment proceeds degrading the quality of the ultrasound focus.

Accordingly, there is a need for reliable and accurate ways of focusing ultrasound beams and maintaining a high-quality ultrasound focus during the ultrasound procedure.

SUMMARY

The present invention provides systems and methods for automatically focusing ultrasound beams that traverse tissue (such as a human skull) having an irregular structure, shape, density, and/or thickness onto a target region prior to and/or during an ultrasound procedure. For ease of reference, the following description only refers to an ultrasound treatment procedure; it should be understood, however, that the same approaches generally apply as well to an ultrasound imaging procedure. In addition, although the description herein refers to ultrasound beams traversing a human skull only, the auto-focusing approach described in connection with various embodiments may be applied to determine beam aberrations resulting from any part of the human body, such as ribs, thereby allowing the transducer parameter values (e.g., phase shifts and/or amplitudes) to be adjusted to compensate for the aberrations.

In various embodiments, the auto-focusing procedure prior to ultrasound treatment is achieved using microbubbles introduced parenterally by an administration system. Because the microbubbles encapsulate gas, the bubble surfaces may collectively form an ultrasound reflector. By analyzing the reflections from the microbubbles, the beam aberrations resulting from the traversed tissue may be determined; subsequently, the transducer parameter values (e.g., phase shifts and/or amplitudes) may be adjusted in order to compensate for the aberrations, thereby establishing a high-quality focus properly located at the target region. In addition, through iterative cycles of measurement and adjustment as ultrasound is reflected from the microbubbles, the high-quality focus can be reliably maintained at the target region.

Using microbubbles introduced by the administration system may advantageously allow focus-assisting reflections to be acquired from low-power ultrasound waves. As a result, this approach avoids undesired damage to the target and/or non-target regions that may result from application of high-power ultrasound waves. In some embodiments, auto-focusing is performed utilizing microbubbles generated by the ultrasound waves prior to the ultrasound procedure. Although high-power ultrasound waves are typically required to generate the microbubbles, because the auto-focusing procedure may be relatively brief—e.g., occurring over a duration of several milliseconds or less—heating in the target and/or non-target tissue caused by the auto-focusing procedure may be minimized. In addition, using microbubbles generated by the ultrasound waves may advantageously reduce system complexity by obviating the need for a microbubble administration system.

During the ultrasound treatment, ultrasound transmission may be halted periodically (e.g., every 5 seconds) to perform auto-focusing so as to ensure that changes in acoustic properties of the traversed tissue resulting from the treatment itself are timely identified and compensated for. For example, a series of short ultrasound pulses (e.g., having a duration of 3 milliseconds) having a ramped-up power may be employed to identify a cavitation threshold regime in which the sonications cause generation of stable, low-energy oscillations (also called stable cavitation) of the microbubbles without creating significant clinical effects (i.e., no or limited temperature increase in the target and/or non-target regions that can otherwise result from cavitation). The transducer may then transmit to the microbubbles ultrasound energy at a power level within the identified cavitation threshold regime; reflections from the microbubbles may then be analyzed for auto-focusing as described above. Alternatively, the administration system may introduce a low dose of the microbubbles into the target region during the treatment; the low-dose microbubbles may cause clinically insignificant effects on the target/non-target tissue while providing sufficient reflections therefrom for auto-focusing. Therefore, the quality of the focus at the target region can be ensured during the entire treatment procedure. In addition, because the auto-focusing procedure is relatively short, the treatment interruption caused by auto-focusing may not significantly affect the treatment time and/or efficiency.

In some embodiments, auto-focusing is performed without interruption of the treatment. For example, the transducer elements may generate ultrasound waves having multiple working frequencies; one of the frequencies may be utilized for treatment and another one(s) for auto-focusing. Additionally or alternatively, the transducer array may be divided into multiple sub-regions that can be separately controllable; some of the sub-regions may continuously perform treatment, while other sub-regions are activated to transmit auto-focusing pulses having a frequency different from that of the treatment pulses.

In various embodiments, the frequency of the ultrasound waves for auto-focusing is different from (e.g., lower than) the frequency of the ultrasound waves for treatment. This may cause the changes in aberrations of the intervening tissue detected using the lower frequency to be different from the actual changes in aberrations during the ultrasound treatment, where higher-frequency ultrasound waves are applied. Accordingly, a physical model and/or a look-up table may be established and employed to convert or map the aberration changes measured at the lower frequency to the aberration changes at the higher frequency. Based on the obtained aberration changes at the higher treatment frequency, ultrasound parameter values (e.g., amplitudes and/or phase shifts) may be adjusted so as to compensate for the change, thereby creating a high-quality focus at the target region 101 for treatment.

Additionally or alternatively, the physical model may predict the aberration changes of the intervening tissue based on the change in temperatures in the intervening tissue. Again, the ultrasound parameter values may then be adjusted based on the predicted aberration changes to compensate therefor.

In various embodiments, the transducer may transmit low-power ultrasound waves to the intervening tissue (e.g., the skull) prior to treatment and receive the waves reflected therefrom. Based on the detected reflections, information (such as a phase difference) associated with the intervening tissue can be obtained. This information can serve as baseline information for the intervening tissue prior to treatment. During the treatment, the transducer may periodically transmit low-power ultrasound waves to the intervening tissue and receive the waves reflected therefrom; again, based on the reflections, information (e.g., the phase difference) associated with the intervening tissue can be obtained. In one implementation, the information measured during treatment is compared against the baseline information measured prior to treatment; the change in the acoustic response of the intervening tissue can then be determined based on the comparison. Consequently, the ultrasound parameter values may be adjusted to compensate for the change.

Accordingly, in one aspect, the invention pertains to a system for generating an ultrasound focus at a target region. In various embodiments, the system includes an ultrasound transducer having multiple transducer elements; and a controller configured to (a) cause the transducer to transmit a series of treatment ultrasound pulses to the target region; (b) cause the transducer to transmit focusing ultrasound pulses to the target region and generate an acoustic reflector therein; (c) measure reflections of the focusing ultrasound pulses from the acoustic reflector; (d) based at least in part on the measured reflections, adjust a parameter value associated with one or more of the transducer elements; and (e) cause the transducer element(s) to generate an ultrasound beam utilizing the adjusted parameter value. The parameter value may include a frequency, a phase, and/or an amplitude of a signal driving the transducer element(s). In one implementation, the system further includes a detector device for measuring the reflections from the acoustic reflector. Additionally or alternatively, the controller may be further configured to cause the transducer elements to measure the reflections from the acoustic reflector. In some embodiments, the system includes an imager and/or a detector device for detecting generation of the acoustic reflector.

In various embodiments, the focusing ultrasound pulses have a value of a constitutive parameter (e.g., a power, a frequency and/or a pulse shape) different from that of the treatment pulses. For example, the frequency of the focusing ultrasound pulses may be lower than that of the treatment pulses. In addition, the controller may be further configured to convert information associated with the measured reflections at the frequency of the focusing ultrasound pulses to corresponding information at the frequency of the treatment pulses. Further, the controller may be configured to computationally convert the information based at least in part on a stored physical model and/or an empirically established, stored look-up table. In some embodiments, the first portion of the focusing ultrasound pulses has a ramped-up power. The controller is configured to (i) determine a cavitation threshold power regime based at least in part on the measured reflections of the first portion of the focusing ultrasound pulses; and (ii) cause the transducer to transmit the second portion of the focusing ultrasound pulses. In one implementation, the power of the second portion of the focusing ultrasound pulses is within the cavitation threshold power regime.

The controller may be further configured to cause the transducer to resume transmission of the treatment pulses after the acoustic reflector dissipates and/or is swept outside the target region. In addition, the controller may be configured to (i) cause the transducer to generate the second focus having an acoustic radiation force; and (ii) use the acoustic radiation force to sweep the acoustic reflector outside the target region. In various embodiments, the controller is further configured to cause the transducer to transmit low-power ultrasound pulses to intervening tissue located between the transducer and the target region; (ii) measure reflections of the low-power ultrasound pulses from the intervening tissue; and (iii) based at least in part on the measured reflections from the intervening tissue, adjust the parameter value associated with the transducer element(s).

In some embodiments, the system includes a temperature-detection device (e.g., a magnetic resonance imaging device) for detecting a temperature at the target region. The controller is further configured to adjust the parameter value associated with the transducer element(s) based at least in part on the detected temperature. In addition, the controller may be further configured to perform, prior to causing the transducer to resume transmission of the treatment pulses using the adjusted parameter value, actions including (f) based on the adjusted parameter value, transmitting updated focusing ultrasound pulses to the acoustic reflector; and (g) repeating (i) measurement of the reflections from the acoustic reflector, (ii) adjustment of the parameter value associated with the transducer element(s), and (iii) transmission of the updated focusing ultrasound pulses to the acoustic reflector until a stopping condition is satisfied. The stopping condition may consist of a phase difference between currently measured reflections and previously measured reflections being below a threshold; and/or a number of iterations exceeding a predetermined limit.

In various embodiments, the controller is further configured to temporarily suspend transmission of the treatment pulses prior to causing the focusing pulses to be transmitted to the target region. In addition, the controller is configured to cause the transducer to resume transmission of the treatment pulses using the adjusted parameter value. In one embodiment, the controller is further configured to terminate transmission of the treatment ultrasound pulses based at least in part on the adjusted parameter value. Further, the focusing pulses may be transmitted to the target during transmission of the treatment pulses. In some embodiments, at least some of the transducer elements are configured to transmit the treatment pulses and the focusing pulses simultaneously. In addition, the ultrasound transducer may include multiple sub-regions, each sub-region having multiple the transducer elements; the controller may be configured to cause different sub-regions of the transducer to transmit the treatment pulses and the focusing pulses.

As used herein, the term "substantially" means±10%, and in some embodiments, ±5% of the peak intensity. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1:
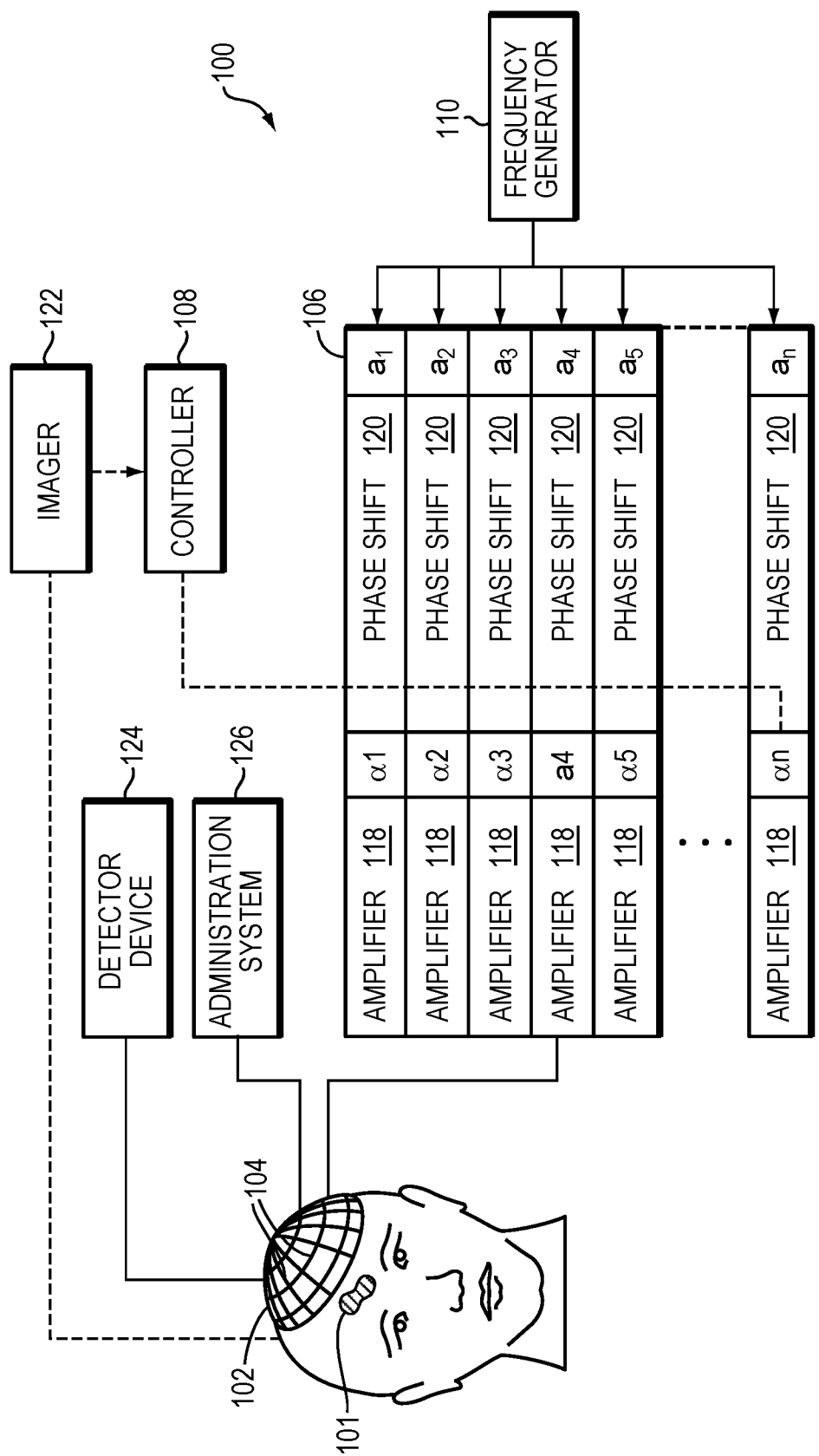
FIG. 1 illustrates a focused ultrasound system in accordance with various embodiments.

FIG. 1 illustrates an exemplary ultrasound system 100 for focusing ultrasound onto a target region 101 through the skull. One of ordinary skill in the art, however, will understand that the ultrasound system 100 described herein may be applied to any part of the human body. In various embodiments, the system 100 includes a phased array 102 of transducer elements 104, a beamformer 106 driving the phased array 102, a controller 108 in communication with the beamformer 106, and a frequency generator 110 providing an input electronic signal to the beamformer 106.

The array 102 may have a curved (e.g., spherical or parabolic) shape suitable for placing it on the surface of the skull or a body part other than the skull, or may include one or more planar or otherwise shaped sections. Its dimensions may vary, depending on the application, between millimeters and tens of centimeters. The transducer elements 104 of the array 102 may be piezoelectric ceramic elements, and may be mounted in silicone rubber or any other material suitable for damping the mechanical coupling between the elements 104. Piezo-composite materials, or generally any materials capable of converting electrical energy to acoustic energy, may also be used. To assure maximum power transfer to the transducer elements 104, the elements 104 may be configured for electrical resonance at 50Ω, matching input connector impedance.

The transducer array 102 is coupled to the beamformer 106, which drives the individual transducer elements 104 so that they collectively produce a focused ultrasonic beam or field. For n transducer elements, the beamformer 106 may contain n driver circuits, each circuit including or consisting of an amplifier 118 and a phase delay circuit 120; drive circuit drives one of the transducer elements 104. The beamformer 106 receives a radio frequency (RF) input signal, typically in the range from 0.1 MHz to 1.0 MHz, from the frequency generator 110, which may, for example, be a Model DS345 generator available from Stanford Research Systems. The input signal may be split into n channels for the n amplifiers 118 and delay circuits 120 of the beamformer 106. In some embodiments, the frequency generator 110 is integrated with the beamformer 106. The radio frequency generator 110 and the beamformer 106 are configured to drive the individual transducer elements 104 of the transducer array 102 at the same frequency, but at different phases and/or different amplitudes.

The amplification or attenuation factors $\alpha_1$-$\alpha_n$ and the phase shifts $\alpha_1$-$\alpha_n$ imposed by the beamformer 106 serve to transmit and focus ultrasonic energy through inhomogeneous tissue (e.g., the patient's skull) onto the target region (e.g., a region in the patient's brain). Via adjustments of the amplification factors and/or the phase shifts, a desired shape and intensity of a focal zone may be created at the target region.

The amplification factors and phase shifts may be computed using the controller 108, which may provide the computational functions through software, hardware, firmware, hardwiring, or any combination thereof. For example, the controller 108 may utilize a general-purpose or special-purpose digital data processor programmed with software in a conventional manner, and without undue experimentation, to determine the frequency, phase shifts and/or amplification factors of the transducer elements 104. In certain embodiments, the controller computation is based on information about the characteristics (e.g., structure, thickness, density, etc.) of the skull and their effects on propagation of acoustic energy. In various embodiments, such information is obtained from an imager 122, such as a magnetic resonance imaging (MRI) device, a computer tomography (CT) device, a positron emission tomography (PET) device, a single-photon emission computed tomography (SPECT) device, or an ultrasonography device. The imager 122 may provide a set of two-dimensional images suitable for reconstructing a three-dimensional image of the skull from which thicknesses and densities can be inferred; alternatively, image acquisition may be three-dimensional. In addition, image-manipulation functionality may be implemented in the imager 122, in the controller 108, or in a separate device.

System 100 may be modified in various ways within the scope of the invention. For example, for diagnostic applications, the system may further include a detector device 124 that measures transmitted or reflected ultrasound, and which may provide the signals it receives to the controller 108 for further processing. The reflection and transmission signals may also provide an alternative or additional source for determination of the phase shifts and/or amplification factors or feedback for the phase and amplitude adjustments of the beamformer 106. The system 100 may contain a positioner for arranging the array 102 of transducer elements 104 with respect to the patient's skull. In order to apply ultrasound therapy to body parts other than the brain, the transducer array 102 may take a different (e.g., cylindrical) shape. In some embodiments, the transducer elements 104 are mounted movably and rotatably, providing mechanical degrees of freedom that can be exploited to improve focusing properties. Such movable transducers may be adjusted by conventional actuators, which may be driven by a component of controller 108 or by a separate mechanical controller.

In addition, the system 100 may further include an administration system 126 for introducing microbubbles into the patient's body for assisting auto-focusing of the ultrasound waves at the target region 101. For example, the microbubbles may be introduced in the form of liquid droplets that subsequently vaporize, as gas-filled bubbles, or entrained with another suitable substance, such as a conventional ultrasound contrast agent. Because of their encapsulation of gas therein, the microbubbles act as reflectors of ultrasound and the reflections therefrom can be used to obtain information about the focusing properties at the target region 101. Examples of suitable administration systems are described in the U.S. Patent Application entitled "Controlling Delivery of Therapeutic Agent in Microbubble-Enhanced Ultrasound Procedures" filed on even date herewith, the contents of which are incorporated herein by reference.

Figure 2:
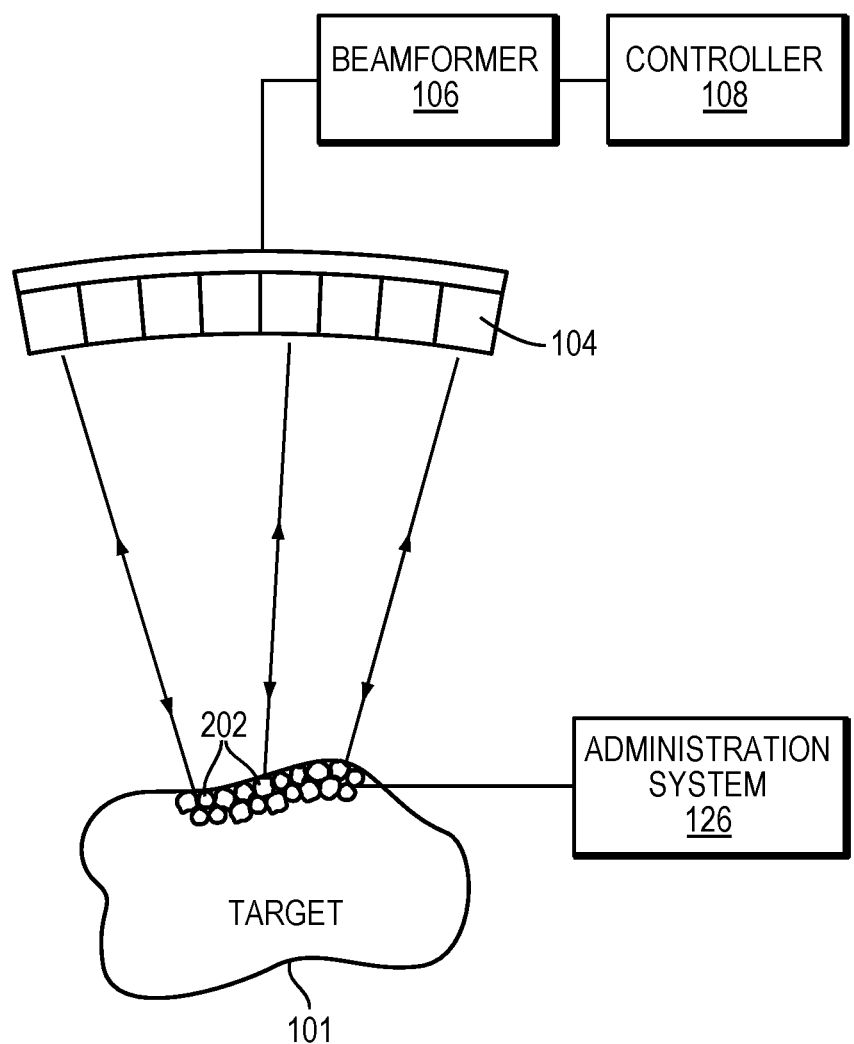
FIG. 2 depicts ultrasound beams delivered to microbubbles in tissue located in a focal zone of the transducer in accordance with various embodiments.

Referring to FIG. 2, in some embodiments, after the microbubbles 202 are administered into the target region 101 (and/or near the target region), the controller 108 activates the transducer elements 104 to transmit ultrasound waves to the microbubbles 202. Ultrasound reflections from the administered microbubbles may be measured using the detector device 124 and/or transducer elements 104, which then transmit the resulting signals to the controller 108. The controller 108 may then analyze the receive signals to obtain information, such as the amplitudes and/or phases, associated with the reflection beams. In one embodiment, the controller 108 compares the phases of the measured reflections, $\varphi_{ref}$, to the phases of the transmitted waves, $\varphi_{tra}$, determines the difference therebetween ($\Delta\varphi=\varphi_{ref}-\varphi_{tra}$), and operates the transducers elements 104 in accordance with the difference; this is herein referred to as "auto-focusing." For example, the controller 108 may cause each transducer element 104 to transmit another ultrasound beam having a phase shift of the determined phase difference, $\Delta\varphi$, to the microbubbles 202 and measure the resulting reflections therefrom. Again, the phase difference between the reflected and transmitted ultrasound may be set as the phase value correction for the next sonication. This process can be iteratively implemented until the phase difference between the reflected and transmitted waves is below a threshold value (e.g., 10°), which indicates that the ultrasound beams focus at the target region 101 with desired focusing properties (e.g., having a desired shape and/or optimal power for thermal treatment). The phase-shift adjusting procedure may be terminated when other conditions are met. For example, the phase-shift adjustment may be stopped when too may iterations (e.g., more than 20 times) have been performed or when the difference between two successive iterations is too small (e.g., $\Delta\varphi_{n+1}-\Delta\varphi_n<5°$).

Accordingly, using microbubbles administered from the administration system 126, a focus having the desired properties may be reliably and accurately generated at the target region 101 prior to and at the beginning of the ultrasound treatment procedure. In addition, because the microbubbles are preformed and injected into the patient's body, low-power ultrasound waves may be sufficient to acquire reflections therefrom. This auto-focusing approach thus avoids undesired damage to the target and/or non-target regions resulting from high-power sonications.

Additionally or alternatively, the auto-focusing procedure may be performed utilizing microbubbles generated by the ultrasound waves. For example, referring FIG. 2 again, the controller 108 may cause the beamformer 106 to provide drive signals to the transducer elements 104 above an intensity threshold such that the acoustic energy emitted by the transducer elements 104 generates microbubbles 202 in the liquid contained in the tissue. The microbubbles can be formed due to the negative pressure produced by the propagating ultrasonic waves or when the heated liquid ruptures and is filled with gas/vapor. Approaches to determining the intensities and/or phase shifts of the ultrasound waves necessary to generate the microbubbles in the focal zone are provided in U.S. Patent Application No. 62/366,200 (PCT Appl. No. PCT/IB2017/000990), the entire disclosure of which is incorporated herein by reference.

Generally, high-power ultrasound waves (i.e., above the threshold level of microbubble generation) may be required to generate the microbubbles. However, because the auto-focusing procedure may be relatively brief (e.g., occurring over a duration of several milliseconds or less) and the thermal response of the tissue may not be immediate (e.g., there is a lag time between the acoustic energy deposition and tissue temperature increase), the temperature increase of the target and/or non-target tissue resulting from the high-power ultrasound waves utilized for generating the microbubbles may be sufficiently small to be clinically insignificant or at least acceptable (e.g., less than a predetermined threshold). In addition, the formation of the microbubbles 202 and the condition of the target and/or non-target regions may be monitored in real time using the imager 122, the ultrasound detector device 124 and/or other suitable devices, and consequently, damage to the target/non-target region may be timely identified and thereby minimized. Further, utilizing ultrasound waves to create microbubbles may advantageously reduce system complexity by obviating the need for the administration system 126.

In various embodiments, after the focusing process is complete, the first treatment ultrasound transmission is delayed to allow the microbubbles 202 to at least partially dissipate and/or collapse in order to avoid damage to non-target tissue resulting from cavitation. If ultrasound contrast agents are introduced for microbubble formation during the focusing process, treatment may be postponed until the generated microbubbles substantially collapse or at least until the enhanced ultrasound energy absorption that they cause are minimized. Alternatively or additionally, the controller 108 may cause the beamformer 106 to provide drive signals to the transducer elements 104 to generate a focus (e.g., a point focus, a line focus or any suitable shape of focus) at the microbubble location to sweep the microbubbles away from the target region 101. Approaches for sweeping the microbubbles from one location to another location are provided in U.S. patent application Ser. No. 15/265,204, the entire content of which is incorporated herein by reference.

In various embodiments, after the microbubbles 202 dissipate and/or are swept away from the target region 101, the controller 108 activates the transducer elements 104 based on the parameter values determined in the auto-focusing procedure to treat the target region 101. During the treatment, ultrasound energy may be deposited into the intervening tissue (e.g., the skull) located between the target and the transducer; this may cause the acoustic properties of the intervening tissue to change. As a result, the ultrasound wave attenuations and distortions caused by the intervening tissue may vary as the treatment proceeds, so that the ultrasound parameter values determined based on the unheated intervening tissue in the auto-focusing procedure performed prior to treatment no longer generate a focus having the desired properties.

Figure 3A:
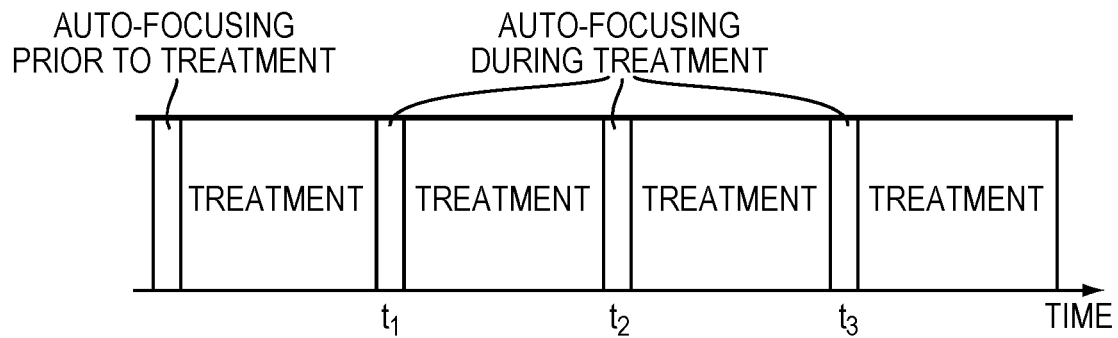
FIG. 3A illustrates an auto-focusing procedure performed prior to and during ultrasound treatment in accordance with various embodiments.
Figure 3B:
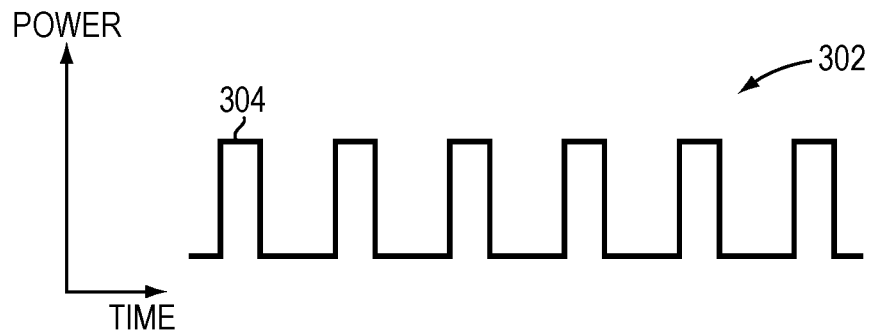
FIGS. 3B-3E depict various configurations of the ultrasound pulses utilized in an auto-focusing procedure in accordance with various embodiments.
Figure 3C:
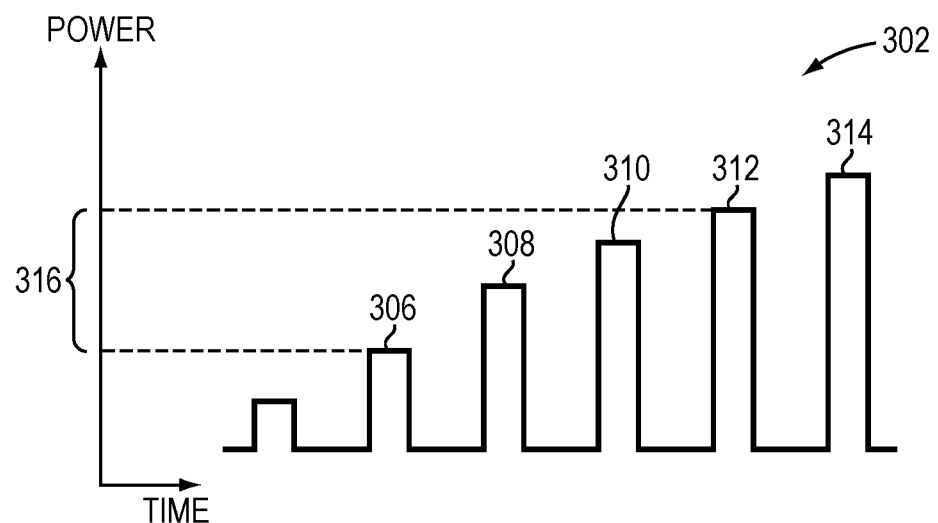

To solve this problem, with reference to FIG. 3A, in various embodiments, the ultrasound treatment is periodically halted (e.g., every 5 seconds) for performing an auto-focusing procedure so as to ensure that the changes in acoustic properties of the traversing tissue are timely identified and compensated for. Referring to FIG. 3B, in one embodiment, the auto-focusing procedure during the treatment is performed by transmitting a series of short ultrasound pulses 302 (e.g., having a duration of 3 milliseconds) to the target region 101. The first pulse 304 of the series of pulses 302 may have the same power used in the auto-focusing procedure performed prior to ultrasound treatment. Due to the change in acoustic properties of the traversed tissue, the power sufficient to generate microbubbles in the focal zone (which is at or near the target region 101) may be different. Accordingly, referring to FIG. 3C, in some embodiments, the power of the ultrasound pulses 302 is ramped up to identify a cavitation threshold regime where the power of the ultrasound waves causes generation of microbubbles having limited stable cavitation and without forming a cloud. For example, at pulse 306, the ultrasound may start to form microbubbles in the tissue. At pulses 308-312, the ultrasound power causes the microbubbles to have gentle stable cavitation that has insignificant, acceptable or desired clinical effects on the tissue. This condition can be inferred from the temperature of the target/non-target tissue monitored by the imager 122 and/or the acoustic response of the microbubbles detected by the detector device 124. For example, the effect of cavitation on the tissue may be considered gentle if, for example, the temperature increase in the target/non-target region is below a predetermined threshold and/or the amplitude of the acoustic signals from the microbubbles is below a predetermined threshold. At pulse 314, the microbubbles may form a cloud having stable cavitation or transient cavitation that causes clinically significant effects on the tissue (e.g., the temperature increase at the target/non-target tissue is above the predetermined threshold and/or the amplitude of the acoustic signals from the microbubbles is above the predetermined threshold). Given this response profile, the cavitation threshold regime 316 may be identified as having a power range between the power of the pulse 306 and pulse 312.

Once the cavitation threshold regime 316 is identified, the transducer 102 is operated to produce ultrasound at a power level in the regime 316 for auto-focusing. For example, ultrasound waves having the power of pulse 310 may be transmitted to create the microbubbles; subsequently, ultrasound reflections from the microbubbles may be detected and analyzed for auto-focusing as described above. Alternatively, the administration system 126 may introduce a low dose of the microbubbles into the target region during the treatment; the low-dose microbubbles may cause clinically insignificant effects on the target/non-target tissue while providing sufficient reflections therefrom for auto-focusing. Again, after the auto-focusing process is complete and the microbubbles dissipate and/or are swept away from the target region 101, ultrasound treatment may be resumed. In one embodiment, the resumed ultrasound transmission has transducer parameter values updated based on the auto-focusing procedure performed during the treatment suspension. Accordingly, using low-power ultrasound waves to generate microbubbles and performing the auto-focusing procedure periodically during the ultrasound treatment may ensure that the focus retains the desired qualities during the entire treatment, notwithstanding the change in the acoustic properties of the intervening tissue. In addition, because the auto-focusing procedure is relatively short (e.g., less than 100 milliseconds), the treatment time and/or efficiency affected by the auto-focusing procedure is not significant.

Figure 3D:
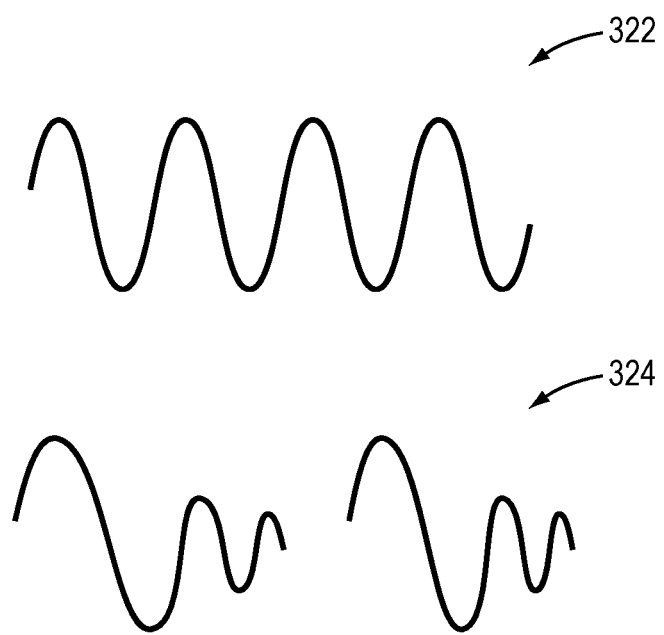
Figure 3E:
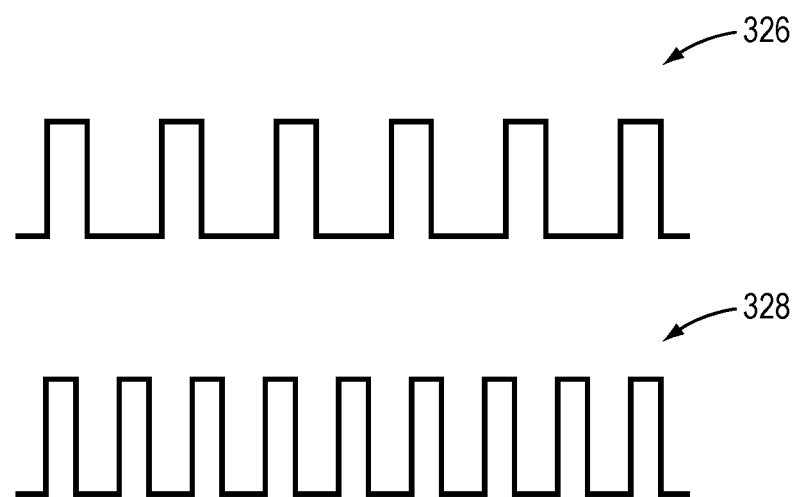

Generally, the shape and frequency of the ultrasound waves used in the auto-focusing procedure is the same as that used in the treatment procedure. But this is not necessarily the case. For example, referring to FIG. 3D, the ultrasound waves 322 that are lightly damped and have a narrow bandwidth may be applied for treatment, while the ultrasound waves 324 that are heavily damped and have a wide bandwidth may be utilized for auto-focusing. Alternatively, the waves 322 may be utilized for auto-focusing, while the waves 324 may be applied for treatment. In addition, referring to FIG. 3E, the frequency of the ultrasound pulses 326 for auto-focusing may be lower than the frequency of the ultrasound pulses 328 for the treatment. Because a longer pulse period means more time to create microbubbles from gas dissolved in the tissue, applying low-frequency ultrasound pulses may advantageously increase the likelihood of causing the microbubbles to be formed and/or cavitate in the tissue. In some embodiments, ultrasound reflections from the microbubbles in the current auto-focusing procedure (e.g., at time $t_2$ in FIG. 3A) are compared to the reflections obtained in the previous auto-focusing procedure (e.g., at time $t_1$ in FIG. 3A); based thereon, the change in the aberrations of the intervening tissue and/or the change in beam transmissions through the intervening tissue resulting from the ultrasound treatment performed during $t_1$ and $t_2$ can be determined. In one implementation, ultrasound parameter values (e.g., amplitudes and/or phases) are updated to compensate for the determined change in the beam aberration/transmission.

The change in aberration detected using the lower frequency may be the same or different from the actual aberration change occurring during ultrasound treatment when the higher frequency is applied. In some embodiments, a physical model converting the aberration change at the lower frequency to that at the higher frequency is established prior to the auto-focusing and treatment procedures. The aberration change at the higher treatment frequency may then be utilized to update the ultrasound parameter values during treatment. In one embodiment, the physical model is established as follows. First, predicted beam paths from the transducer elements 104 to the target region 101 are obtained based on the geometric arrangement (e.g., the relative location and/or orientation of the intervening tissue with respect to the target region 101 and/or the transducer 102). Additionally, the physical model may include parameters, such as material properties (e.g., the energy absorption of the tissue at the lower and higher frequencies or the speed of sound) along the beam path. The material properties may be collected using the imager 122 as described above and/or other suitable devices. For example, if the intervening tissue is a patient's skull, CT imaging may be used to extract the anatomical characteristics (such as the skull thickness, skull layers, local bone densities and/or directional or geometrical features including a normal relative to a surface region or an approximated curvature) of the skull. Methods of creating a local geometric model or mapping of the skull are described, for example, in U.S. Patent Publication No. 2010/0179425, the entire disclosure of which is hereby incorporated by reference. In addition, the structural inhomogeneity of the skull may be characterized using an indicator that can be quantified at the microstructure level of the skull; the indicator is determined based on the skull density measured in images acquired using an imager 122. A suitable method is described in U.S. Patent Publication No. 2016/0184026, the entire disclosure of which is hereby incorporated by reference.

Based on the predicted beam paths and material properties of the intervening tissue, the physical model may be used to analyze acoustic paths through the intervening tissue. Using the physical model, simulations may be performed to predict how the skull will reflect and/or absorb ultrasound energy having different frequencies at various temperatures. Consequently, the physical model may be used to derive a transfer function relating the aberration change at one frequency (e.g., the lower, auto-focusing frequency) to that at another frequency (e.g., the higher, treatment frequency).

Figure 3F:
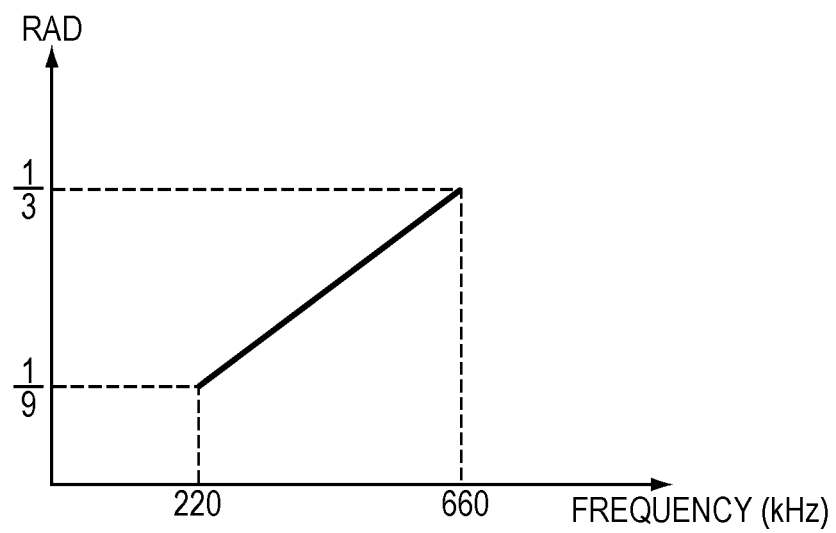
FIG. 3F depicts a relationship between the ultrasound frequency and aberration change of an intervening tissue in accordance with various embodiments.

Alternatively or additionally, a transfer function or look-up table mapping the aberration change at the lower frequency to the higher frequency may be empirically determined based on reflection waves received from the same or different patients prior to the auto-focusing and treatment procedures. In some embodiments, the aberration change is dependent on the frequency. For example, referring to FIG. 3F, when the frequency increases by a factor of 3 from 220 kHz to 660 kHz, the aberration change may also increase from ⅑ rad to ⅓ rad. This linear relationship may be useful for aberration conversion particularly when the change is small (e.g., less than 1 rad).

In some embodiments, the physical model predicts the aberration change of the intervening tissue based on a temperature change. For example, by analyzing the material properties of the intervening tissue along the beam paths and the responses of the material properties to the temperature change, the physical model may predict the change in acoustic properties of the intervening tissue and consequently the change in beam aberrations associated therewith. In this case, the physical model may predict the aberration change at the treatment frequency, so no conversion between different frequencies is necessary. Once again, after the aberration change resulting from the temperature increase of the treatment is obtained, the controller 108 may adjust the ultrasound parameter values to compensate therefor.

The temperature change in the intervening tissue may be measured using the imager 122 and/or other suitable devices. For example, MR thermometry (or MR thermal imaging) may provide a non-invasive means of quantitatively monitoring in vivo temperatures. Details regarding measuring the temperature of target tissue may be found in U.S. Pat. Nos. 8,368,401 and 9,289,154, the entire disclosures of which are hereby incorporated by reference. In some embodiments, the temperature of the intervening tissue is estimated using the physical model. For example, the physical model may analyze the acoustic paths through the intervening tissue and perform thermal simulations to estimate how the intervening tissue reflects and/or absorbs different quantities of energy and have different heating profiles and subsequently predict the temperature distribution in the intervening tissue.

In various embodiments, prior to treatment, the transducer 102 transmits low-power ultrasound waves to the intervening tissue (e.g., the skull) and receives the waves reflected therefrom. The controller 108 then analyzes the measured reflection signals to obtain information (such as a phase difference) about the transmission and reflection of the ultrasound waves resulting from the intervening tissue. This information is provided as baseline information associated with the intervening tissue. The baseline information may be stored in memory along with the aberrations measured in the auto-focusing procedure performed prior to treatment. During the ultrasound treatment, the transducer 102 may periodically transmit the low-power ultrasound waves to the intervening tissue and receive the waves reflected therefrom. The controller 108 may then analyze the received reflections to obtain information (e.g., the phase difference) associated with the intervening tissue, compare the information to the baseline information, and determine a difference therebetween. This difference may provide supplemental or revised information about the change in aberrations of the intervening tissue caused by the treatment. Again, the ultrasound parameter values may then be adjusted based on the difference of phase differences (or, in some embodiments, together with the aberration change measured in the auto-focusing procedure) so as to generate a high-quality focus at the target region 101.

Figure 4A:
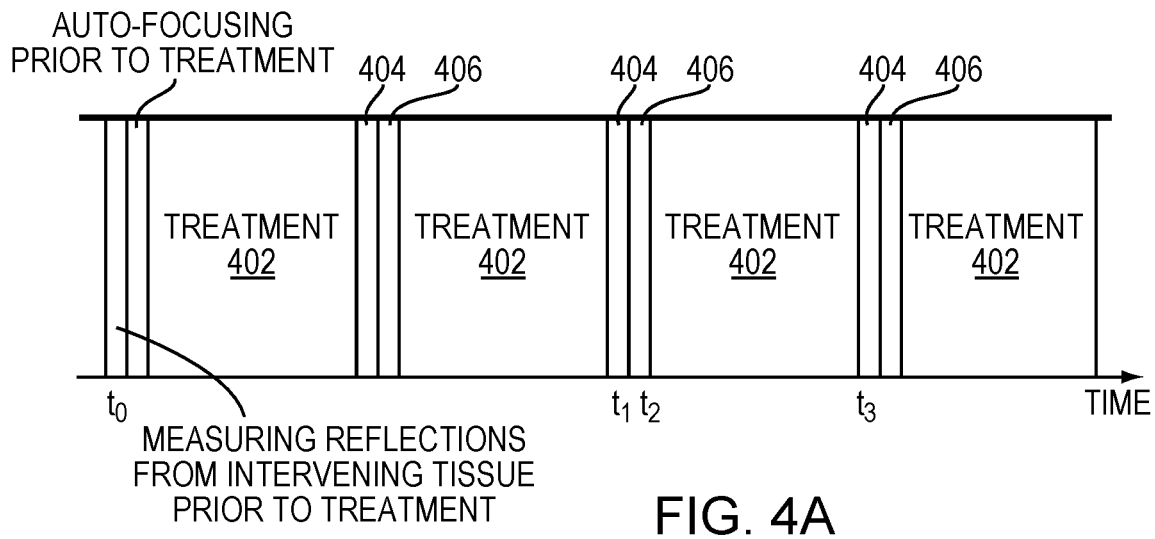
FIGS. 4A-4C illustrate approaches for performing an auto-focusing procedure and measurements of ultrasound reflections off the intervening tissue located between a transducer and a target in accordance with various embodiments.
Figure 4B:
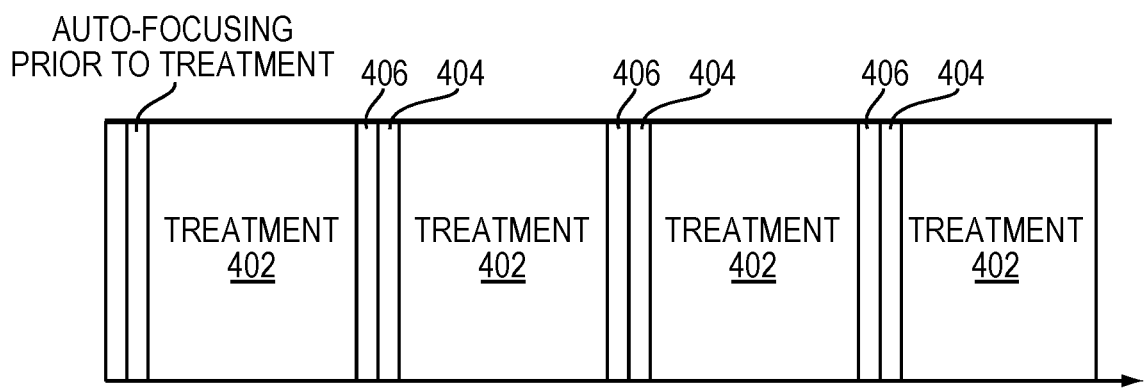
Figure 4C:
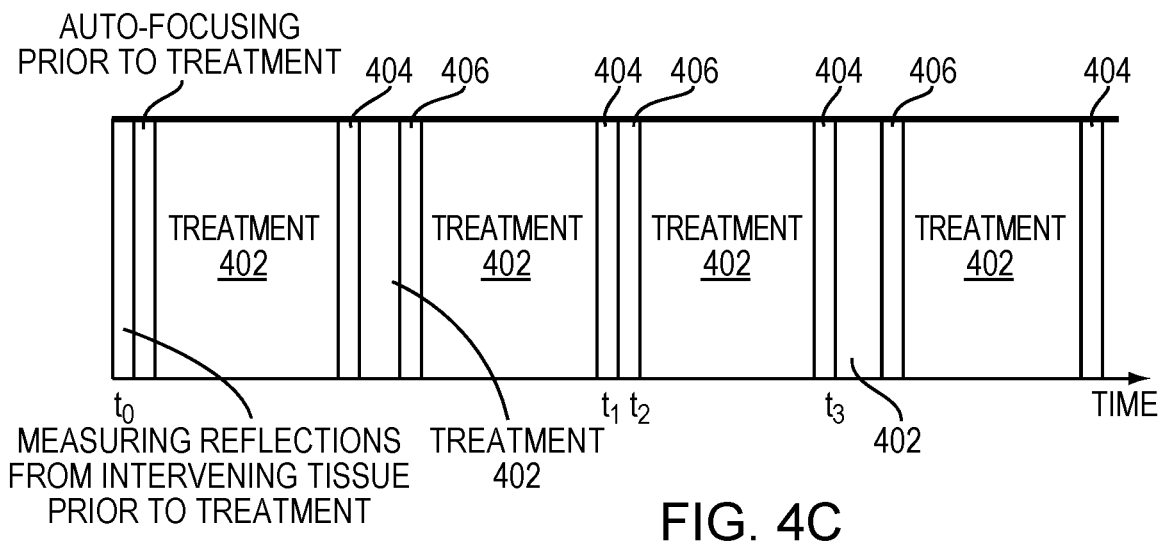

Measurements of the reflections from the intervening tissue may be synchronized with the auto-focusing procedure during treatment. For example, referring to FIG. 4A, after the treatment sonications 402 are suspended, the measurements 404 of the reflections from the intervening tissue may be performed prior to the auto-focusing procedure 406. Alternatively, the measurements 404 may be performed after the auto-focusing procedure 406 (FIG. 4B). In some embodiments, the measurements 404 of the reflections from the intervening tissue are performed independent of and unsynchronized with the auto-focusing procedure (FIG. 4C). In addition, the phase difference obtained in the current measurement (e.g., at time $t_1$) may be stored alone or along with the aberration change measured in the respective auto-focusing procedure (e.g., at time $t_2$) in the memory. The phase difference obtained in the subsequent measurement (e.g., at time $t_3$) may be compared against the phase difference in the preceding measurement (e.g., at time $t_1$) or baseline measurement (e.g., at time to) to determine the difference therebtween. This difference may provide supplemental or revised information about the change in aberrations of the intervening tissue caused by the treatment. Based on the determined difference, the ultrasound parameter values may then be adjusted so as to retain the focusing qualities at the target region 101. In some embodiments, the determined difference is above a predetermined threshold, which indicates that a safety-related issue may have occurred (e.g., the skull properties may have changed beyond a safe level). In this situation, the ultrasound treatment may be terminated or suspended.

In some embodiments, the auto-focusing is performed without interruption of the treatment. For example, the transducer elements may generate ultrasound waves having multiple working frequencies, one of which is optimized for treatment and another of which may be utilized for auto-focusing. Again, the auto-focusing frequency is typically lower than the treatment frequency as a longer pulse period may increase the likelihood of microbubble generation. In some embodiments, more than one frequency can be utilized for auto-focusing. For example, the ultrasound waves having a low frequency, $f_1$, may be transmitted to the target to initiate microbubble generation; subsequently, the waves having a higher frequency, $f_2$, ($f_2 > f_1$) may be transmitted to the target to facilitate auto-focusing as described above. Frequencies $f_1$ and $f_2$ may be different from (e.g., lower than) the treatment frequency, $f_3$. Because the self-created microbubbles (i.e., generated via application of the waves having the frequency $f_1$) typically dissipate and/or collapse much faster (e.g., in less than 3 seconds), there is no (or at least limited) microbubble cavitation effect on the target region. In this way, the transducer elements 104 may continuously transmit ultrasound waves having multiple frequencies to the target region during treatment and the elements 104 and/or detector device 124 may continuously or periodically (e.g., every 5 seconds) be activated to receive ultrasound reflections from the microbubbles. The received reflections may be filtered using any suitable analog or digital filter to extract the signals having the auto-focusing frequency (e.g., $f_2$). Subsequently, the controller 108 may analyze the extracted signals to obtain information (e.g., phase shifts) associated with the intervening tissue, compare the information to the baseline information, and determine a difference therebetween. Again, this difference may provide supplemental or revised information about the change in aberrations of the intervening tissue caused by the treatment. The transducer parameter values (e.g., phase shifts and/or amplitudes) may then be adjusted in order to compensate for the aberrations. Systems and methods for manufacturing and configuring the transducer to provide multiple working frequencies are described, for example, in U.S. Patent Publ. No. 2016/0114193, the entire disclosure of which is hereby incorporated by reference.

Additionally or alternatively, auto-focusing may be performed during treatment without interruption thereof by dividing the transducer array into multiple sub-regions that can be separately controlled; some of the sub-regions may continuously transmit waves for treatment, while other sub-regions may transmit waves that have a frequency different from (e.g., lower than) that of the treatment pulses for auto-focusing as further described below.

Figure 5A:
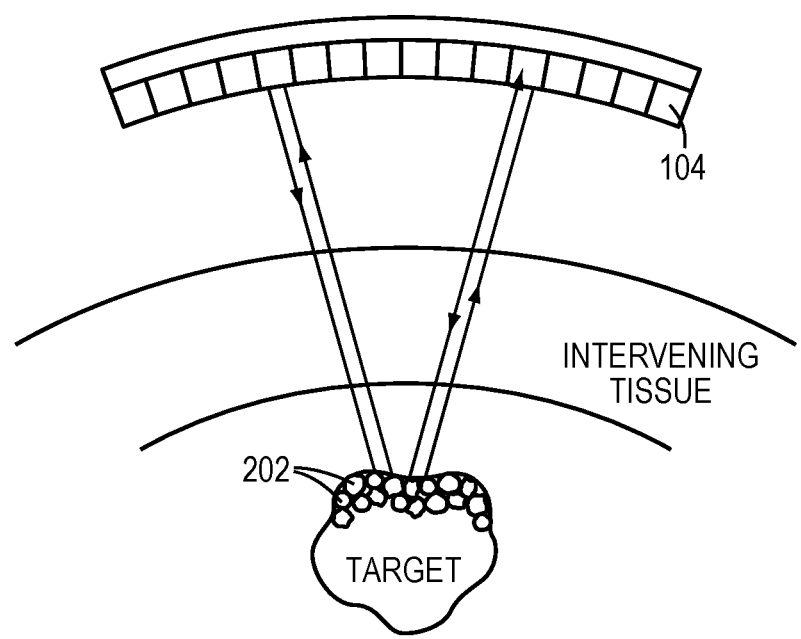
FIGS. 5A-5C depict various configurations of the transducer elements performing an auto-focusing method in accordance with various embodiments.

The reflections from the intervening tissue may be detected by the detector device 124. Alternatively, the transducer elements 104 may possess both transmit and detect capabilities. For example, referring to FIG. 5A, each individual transducer element may alternate between transmitting ultrasound signals to the intervening tissue and/or microbubbles and receiving ultrasound signals reflected therefrom. In one embodiment, all transducer elements 104 substantially simultaneously transmit ultrasound to the intervening tissue/microbubbles and subsequently receive echo signals therefrom.

Figure 5B:
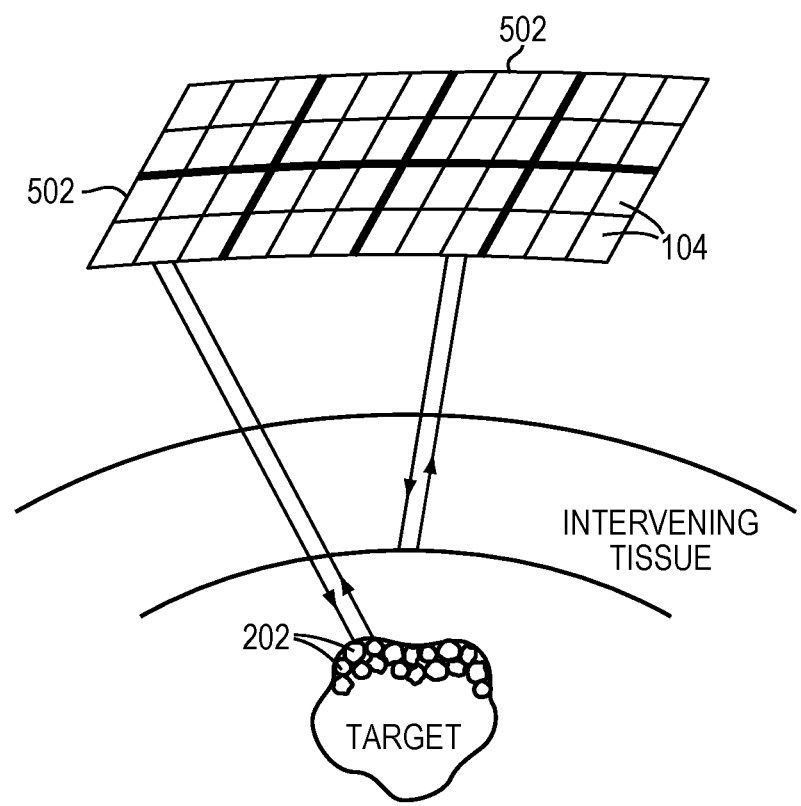
Figure 5C:
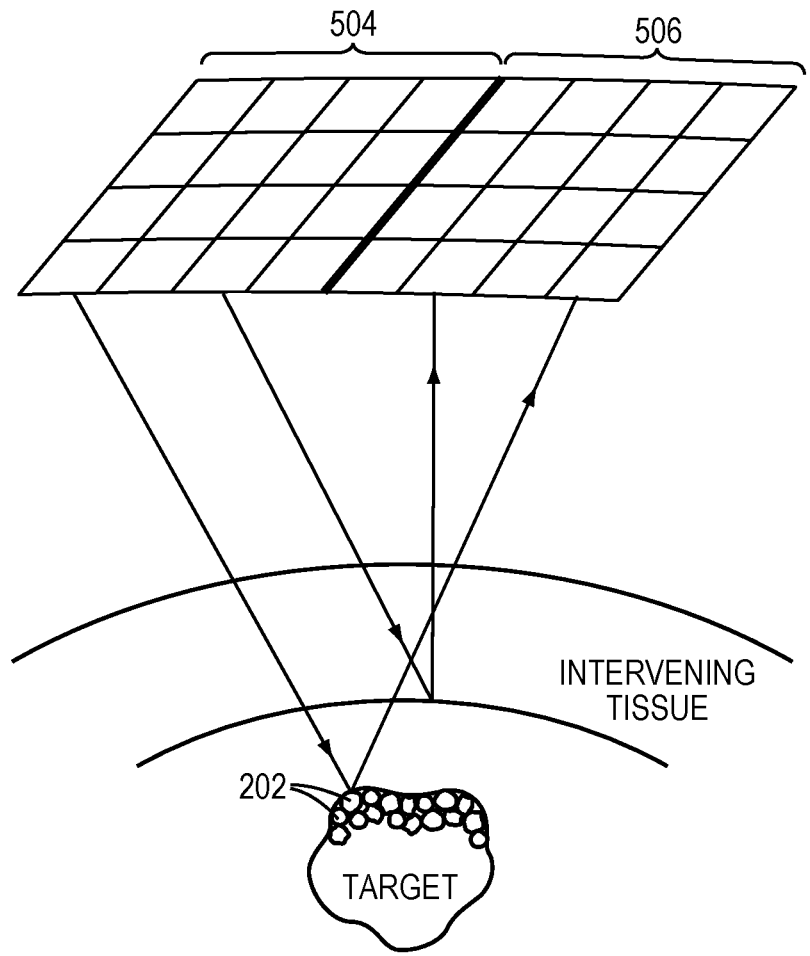

Referring to FIG. 5B, in one implementation, the transducer array is divided into multiple sub-regions 502; each sub-region 502 comprises or consists of a one- or two-dimensional array (i.e., a row or a matrix) of transducer elements 104. The sub-regions 502 may be separately controllable, i.e., they are each capable of (i) emitting ultrasound waves at frequencies, amplitudes and/or phases that are independent of the frequencies, amplitudes and/or phases of the other sub-regions 502, and/or (ii) measuring waves reflected from the microbubbles and/or intervening tissue. In one embodiment, the sub-regions 502 are assigned different frequencies, amplitudes and/or phases from one another, and activated, one at a time, to transmit ultrasound to and receive reflections from the microbubbles and/or intervening tissue. In addition, this configuration may be utilized to perform auto-focusing without interruption of the treatment as described above. For example, some of the sub-regions 502 may continuously transmit treatment pulses to the target for treatment, and other sub-regions 502 may transmit pulses having a frequency different from (e.g., lower than) that of the treatment pulses for auto-focusing. Selection of the sub-regions for performing the auto-focusing and treatment may be fixed or changed based on, for example, the location of the tissue that has been disrupted during the treatment. Referring to FIG. 5C, in another embodiment, the transducer array is divided into a transmit region 504 and a receive region 506; transducer elements in the transmit region 504 transmit the ultrasound waves while transducer elements in the receive region 506 receive the reflected waves. The received reflected waves are then transmitted to the controller 108 for analysis. The transmit region 504 and receive region 506 of may be configured in different patterns and shapes at various locations of the transducer array.

Figure 6A:
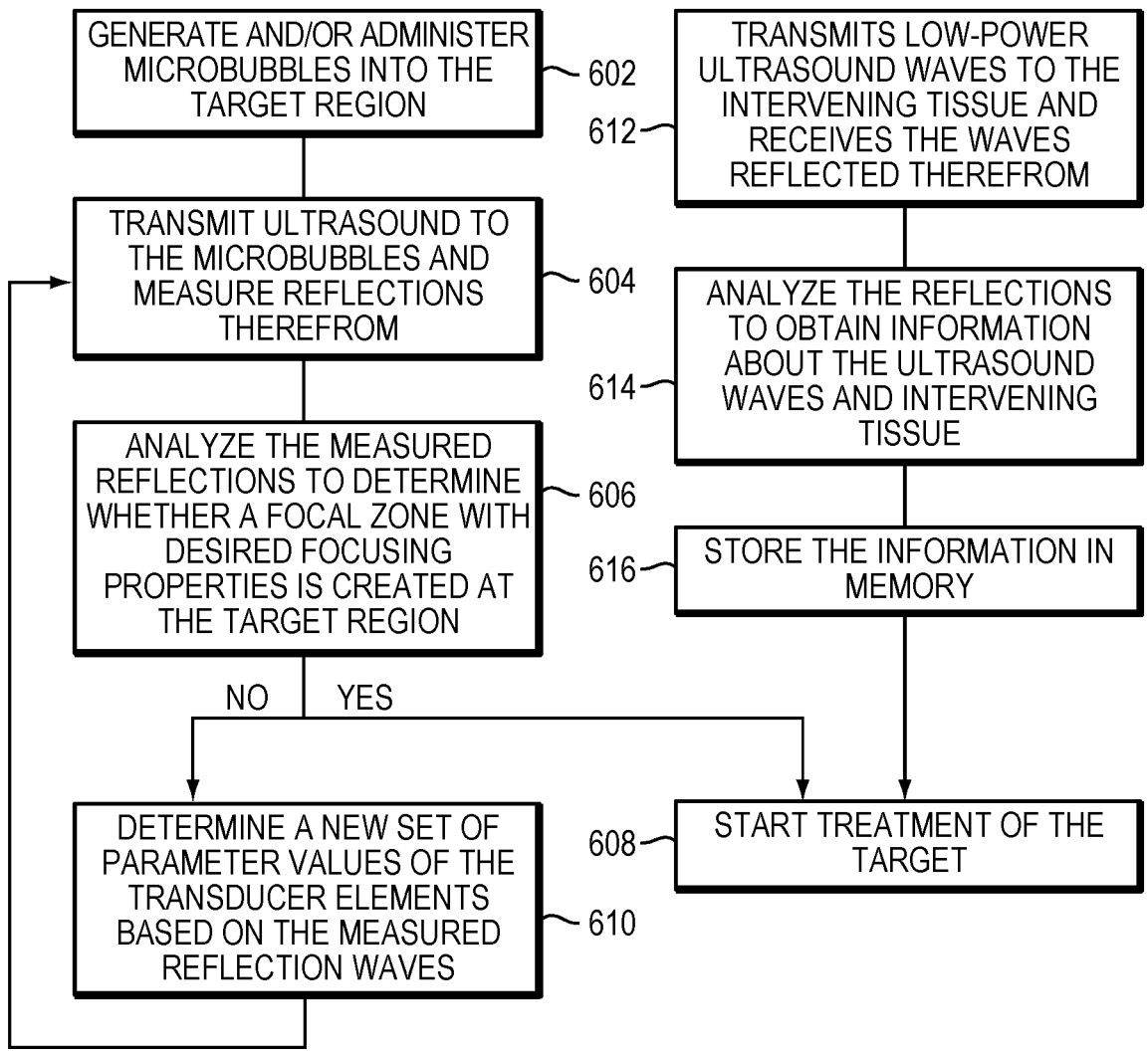
FIGS. 6A and 6B are flow charts illustrating an ultrasound auto-focusing approach performed prior to and during the treatment, respectively, in accordance with various embodiments.
Figure 6B:
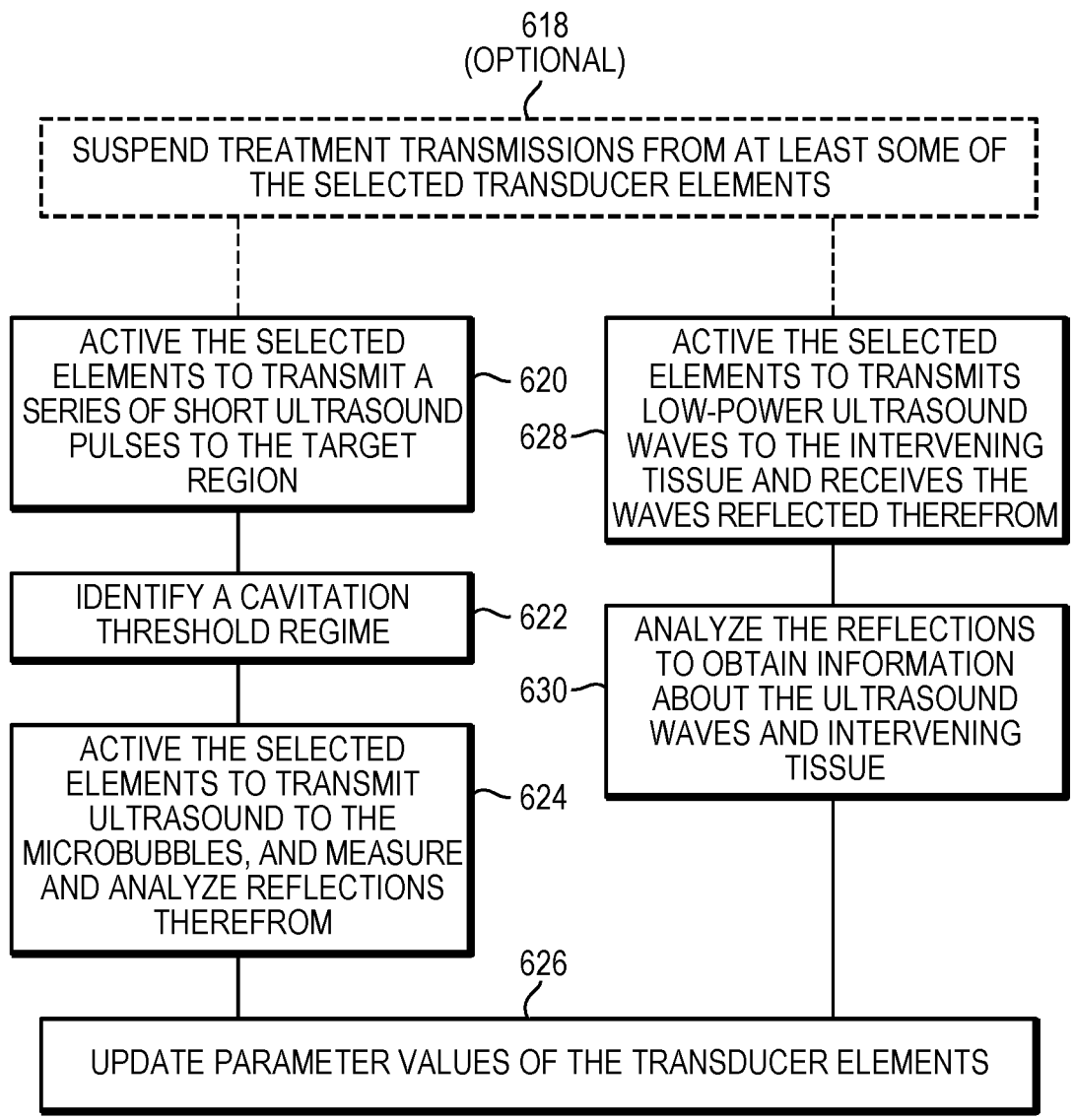

FIGS. 6A and 6B are flow charts illustrating an ultrasound auto-focusing approach performed prior to and during the treatment, respectively, in accordance with various embodiments. In a first preparatory step 602, microbubbles are generated and/or administered into the target region prior to performing the ultrasound treatment. In a second preparatory step 604, ultrasound is transmitted from the transducer elements 104 to the microbubbles, and reflections from the microbubbles are measured. In a third preparatory step 606, the measured reflections are analyzed to determine whether a focal zone with desired focusing properties is created at the target region. If so, the transducer elements transmit ultrasound waves based on the current transducer parameter values (e.g., frequencies, phase shifts and/or amplitudes) to start treatment of the target (step 608). If not, a new set of parameter values of the transducer elements is determined based on the measured reflection waves (step 610), and the ultrasound elements apply the new set of values to direct waves to the microbubbles. Steps 604, 606, 610 are then repeated until desired focusing properties are achieved at the target region. In each iteration, the ultrasound waves may be transmitted to the same or different microbubbles from those in the previous iteration(s); as a result, the reflections received in two iterations may be from the same or different microbubbles. Accordingly, this approach allows the ultrasound beams to auto-focus at the target region prior to treatment despite the presence of inhomogeneous intervening tissue. In some embodiments, the transducer transmits low-power ultrasound waves to the intervening tissue (e.g., the skull) and receives the waves reflected therefrom (step 612). The wave reflections are then analyzed to obtain information (e.g., phase differences) about the ultrasound waves and intervening tissue (step 614). This information may be optionally stored in memory and provided as baseline information of the intervening tissue (step 616).

During the treatment, therapeutic ultrasound transmissions may be periodically (e.g., every 5 seconds) suspended (step 618) to perform auto-focusing. For example, a series of short ultrasound pulses (each having, e.g., a duration of 3 milliseconds) may be transmitted to the target region 101 (step 620). Suspension of the treatment, however, is not essential. As described above, auto-focusing may be performed without interrupting the treatment, e.g., by using transducer elements capable of transmitting various frequencies of waves and/or by dividing the transducer array into multiple sub-regions. The power, frequency and shape of the focusing ultrasound pulses may be the same as or different from that of the treatment ultrasound pulses/waves. In one implementation, the power of the ultrasound pulses is ramped up to identify a cavitation threshold regime where the sonications cause generation and stable cavitation of microbubbles without creating significant clinical effects (i.e., no or limited damage to the target and/or non-target regions) (step 622). Ultrasound waves having power levels within the identified cavitation threshold regime are transmitted to the microbubbles, and reflections therefrom are measured and analyzed (step 624). In some embodiments, a low dose of the microbubbles is introduced, via the administration system 126, into the target region; the low-dose microbubbles may cause ultrasound pulses transmitted thereto to be reflected. Based on the reflections, parameter values of the transducer elements are updated so as to create a focus having the desired qualities at the target region during treatment (step 626). In some embodiments, the transducer also periodically transmits low-power ultrasound waves to the intervening tissue and receives the waves reflected therefrom (step 628); based on the reflections, information (e.g., phase differences) associated with the intervening tissue can be determined (step 630). The phase differences can then be compared against the information acquired prior to treatment in step 614 (step 632). Based on the comparison, the ultrasound parameters can be adjusted for auto-focusing. Again, if the phase difference is above a predetermined threshold, a safety-related issue may have occurred; consequently, the ultrasound treatment may be terminated or suspended.

The controller 108 may include all necessary hardware components and/or software modules to automatically perform certain functions as described above (e.g., analysis of the reflected signals, comparison of the measured phase to the transmitted phase, and/or adjustments of the phases/amplitudes). Accordingly, the auto-focusing approach as described herein may be performed automatically. As an alternative, the analysis of the reflected signals and/or adjustments of the phases/amplitudes may be partially performed manually by a user to create a high-quality ultrasound focus.

One of ordinary skill in the art will understand that variations in the auto-focusing approach described above are possible and are thus within the scope of the present invention. For example, it may not be necessary to activate a majority of the transducer elements 104 for performing auto-focusing using cavitation bubbles as described herein, and the number of transducer elements activated in each sonication may vary. In addition, the microbubbles 202 may be alternatively generated using a conventional dual-frequency approach—i.e., the ultrasound beams are delivered at one frequency to generate microbubbles 202 in the focal zone, and subsequently delivered at another frequency to start the auto-focusing approach as described above. One of skill in the art will also understand that any variations utilizing microbubbles 202 for auto-focusing ultrasound beams at the target region are within the scope of the present invention.

In addition, it should be noted that although the auto-focusing procedure described herein utilizes microbubbles to reflect ultrasound waves, the ultrasound waves may be reflected using other approaches. For example, the administration system 126 may administer emulsions and/or droplets composed of various liquid perfluorocarbon agents into the target region prior to and/or during the treatment. Initial application of the focusing ultrasound pulses may cause the droplets to vaporize into microbubbles, and subsequent application of the focusing ultrasound pulses may be reflected from the microbubbles. The reflections may be detected and analyzed for auto-focusing as described above.

In general, functionality for performing auto-focusing of ultrasound beams, including, analyzing reflected signals from the microbubbles/intervening tissue, determining new parameter values of the transducer elements and/or adjusting ultrasound operations, as described above, whether integrated within a controller of the imager, and/or an ultrasound system, or provided by a separate external controller, may be structured in one or more modules implemented in hardware, software, or a combination of both. For embodiments in which the functions are provided as one or more software programs, the programs may be written in any of a number of high level languages such as PYTHON, JAVA, C, C++, C#, BASIC, various scripting languages, and/or HTML. Additionally, the software can be implemented in an assembly language directed to the microprocessor resident on a target computer (e.g., the controller); for example, the software may be implemented in Intel 80×86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

In addition, the term "controller" used herein broadly includes all necessary hardware components and/or software modules utilized to perform any functionality as described above; the controller may include multiple hardware components and/or software modules and the functionality can be spread among different components and/or modules.

Certain embodiments of the present invention are described above. It is, however, expressly noted that the present invention is not limited to those embodiments; rather, additions and modifications to what is expressly described herein are also included within the scope of the invention.

What is claimed is:

1. A system for generating an ultrasound focus at a target region, the system comprising:
    an ultrasound transducer comprising a plurality of transducer elements; and
    a controller configured to:
        (a) cause the ultrasound transducer to transmit focusing ultrasound pulses to the target region and generate an acoustic reflector therein;
        (b) measure phases of reflections of the focusing ultrasound pulses from the acoustic reflector;
        (c) based at least in part on the measured phases of the reflections, adjust a phase of transmitted waves from at least one of the plurality of transducer elements; and
        (d) cause said at least one of the plurality of transducer elements to generate an ultrasound beam having the adjusted phase so as to improve focusing properties of the ultrasound beam at the target region.

2. The system of claim 1, further comprising a detector device for measuring the reflections of the focusing ultrasound pulses from the acoustic reflector.

3. The system of claim 1, further comprising at least one of an imager or a detector device for detecting generation of the acoustic reflector.

4. The system of claim 1, wherein the controller is further configured to cause at least one of the plurality of transducer elements to measure phases of the reflections of the focusing ultrasound pulses from the acoustic reflector.

5. The system of claim 1, wherein the focusing ultrasound pulses have a value of a constitutive parameter different from that of the ultrasound beam generated in step (d).

6. The system of claim 5, wherein the constitutive parameter comprises at least one of a power, a frequency or a pulse shape.

7. The system of claim 6, wherein the value of the frequency associated with the focusing ultrasound pulses is lower than that associated with the ultrasound beam generated in step (d).

8. The system of claim 6, wherein the controller is further configured to convert information associated with the reflections at the frequency associated with the focusing ultrasound pulses to corresponding information at the frequency associated with the ultrasound beam generated in step (d), wherein the information comprises at least one of (i) a change in aberrations resulting from intervening tissue located between the ultrasound transducer and the target region or (ii) a change in beam transmissions through the intervening tissue.

9. The system of claim 8, wherein the controller is further configured to computationally convert the information based at least in part on a stored physical model.

10. The system of claim 8, wherein the controller is further configured to computationally convert the information based at least in part on an empirically established, stored look-up table.

11. The system of claim 6, wherein a first portion of the focusing ultrasound pulses has a ramped-up power.

12. The system of claim 11, wherein the controller is further configured to:
    (i) determine a cavitation threshold power regime in which generation of the acoustic reflector does not create significant clinical effects based at least in part on the reflections of the first portion of the focusing ultrasound pulses; and
    (ii) cause the ultrasound transducer to transmit a second portion of the focusing ultrasound pulses,
    wherein the power of the second portion of the focusing ultrasound pulses is within the cavitation threshold power regime.

13. The system of claim 1, wherein the controller is further configured to cause said at least one of the plurality of transducer elements to generate the ultrasound beam after the acoustic reflector dissipates or is swept outside the target region.

14. The system of claim 13, wherein the controller is further configured to:
    cause the transducer to generate a second focus having an acoustic radiation force,
    wherein the acoustic radiation force sweeps the acoustic reflector outside the target region.

15. The system of claim 1, wherein the controller is further configured to:
    based at least in part on the measured phases of the reflections, adjust a parameter value associated with at least one of the plurality of transducer elements, wherein the parameter value comprises at least one of a frequency or an amplitude of a signal driving the at least one of the plurality of transducer elements.

16. The system of claim 1, wherein the controller is further configured to:
    (i) cause the ultrasound transducer to transmit low-power ultrasound pulses to intervening tissue located between the ultrasound transducer and the target region;
    (ii) measure phases of reflections of the low-power ultrasound pulses from the intervening tissue; and
    (iii) based at least in part on the measured phases of the reflections from the intervening tissue, adjust the phase of transmitted waves of at least one of the plurality of transducer elements.

17. The system of claim 1, further comprising a temperature-detection device for detecting a temperature at the target region.

18. The system of claim 17, wherein the controller is further configured to adjust the phase of transmitted waves of the at least one of the plurality of transducer elements based at least in part on the detected temperature.

19. The system of claim 17, wherein the temperature-detection device comprises a magnetic resonance imaging device.

20. The system of claim 1, wherein the controller is further configured to perform, prior to step (d), actions comprising:
    (e) based on the adjusted phase, causing the ultrasound transducer to transmit updated focusing ultrasound pulses to the acoustic reflector; and (f) repeating (i) measuring phases of the reflections from the acoustic reflector, (ii) adjustment of the phase of transmitted waves of at least one of the plurality of transducer elements, and (iii) causing the ultrasound transducer to transmit the updated focusing ultrasound pulses to the acoustic reflector until a stopping condition is satisfied.

21. The system of claim 20, wherein the stopping condition consists of one or more of:

a phase difference between currently measured phases of the reflections and previously measured phases of the reflections being below a threshold; or a number of iterations exceeding a predetermined limit.

22. The system of claim 1, wherein the controller is further configured to temporarily suspend generation of the ultrasound beam.

23. The system of claim 22, wherein the controller is further configured to repeat steps (a)-(c) during the suspension.

24. The system of claim 23, wherein the controller is further configured to terminate generation of the focused beam based at least in part on the adjusted phase.

25. The system of claim 1, wherein the focusing ultrasound pulses are transmitted to the target during generation of the focused beam.

26. The system of claim 1, wherein at least some of the plurality of transducer elements are configured to transmit the ultrasound beam and the focusing ultrasound pulses simultaneously.

27. The system of claim 1, wherein the ultrasound transducer comprises a plurality of sub-regions, each sub-region comprising a plurality of the transducer elements, and the controller is further configured to cause different sub-regions of the transducer to transmit the ultrasound beam and the focusing ultrasound pulses.

* * * * *